(12) United States Patent
Valen

(10) Patent No.: US 6,273,721 B1
(45) Date of Patent: Aug. 14, 2001

(54) DENTAL IMPLANT

(76) Inventor: Maurice Valen, 198-45 Foothill Ave., Holliswood, NY (US) 11423-1611

( * ) Notice: Subject to any disclaimer, the term of this patent is extended or adjusted under 35 U.S.C. 154(b) by 0 days.

(21) Appl. No.: 09/207,069

(22) Filed: Dec. 7, 1998

(51) Int. Cl.[7] .................................................. A61C 8/00
(52) U.S. Cl. ............................................................ 433/174
(58) Field of Search ................................... 433/172, 173, 433/174, 201.1

(56) References Cited

U.S. PATENT DOCUMENTS

| | | | |
|---|---|---|---|
| 3,590,485 | * 7/1971 | Chercheve et al. | 433/174 |
| 4,668,191 | * 5/1987 | Plischka | 433/174 |
| 4,934,935 | * 6/1990 | Edwards | 433/174 |
| 4,976,739 | * 12/1990 | Duthie, Jr. | 433/174 |
| 5,007,835 | 4/1991 | Valen . | |
| 5,061,181 | * 10/1991 | Niznick | 433/174 |
| 5,259,398 | * 11/1993 | Vrespa | 433/174 |
| 5,588,838 | * 12/1996 | Hansson et al. | 433/174 |
| 5,628,630 | 5/1997 | Misch et al. . | |

* cited by examiner

Primary Examiner—Nicholas D. Lucchesi
(74) Attorney, Agent, or Firm—Salzman & Levy

(57) ABSTRACT

An improved screw-type implant is designed to be in dynamic equilibrium relative to forces generated at the implant site for bone lamination and osteocompression within physiologic limits. The threads of a selected implant vary in size and pitch relative to the modulus of elasticity for a particular bone region where the implant is to be placed together with a mechanical apparatus for abutment splinting and for an immediate clinical implant fixation.

17 Claims, 7 Drawing Sheets

| Static Compressive Strength of Maxillary Cancellous Bone 10 MPa | |
|---|---|
| Applied Force (In Pounds) | Required Implant Load Bearing Area (LBA) 0.444 MM² |
| 1 | 2.220 |
| 5 | 4.445 |
| 10 | 6.670 |
| 15 | 8.900 |
| 20 | 11.120 |
| 25 | 13.350 |
| 30 | 15.570 |
| 35 | 17.790 |
| 40 | 20.020 |
| 45 | 22.240 |
| 50 | 24.470 |
| 55 | 26.690 |
| 60 | 28.910 |
| 65 | 31.140 |
| 70 | 33.360 |
| 75 | 35.590 |
| 80 | 37.810 |
| 85 | 40.040 |
| 90 | 42.260 |
| 95 | 44.480 |

| Static Compressive Strength of Maxillary Cancellous Bone 15 MPa | |
|---|---|
| Applied Force (In Pounds) | Required Implant Load Bearing Area (LBA) 0.296 MM² |
| 1 | 1.480 |
| 5 | 2.970 |
| 10 | 4.450 |
| 15 | 5.930 |
| 20 | 7.410 |
| 25 | 8.900 |
| 30 | 10.380 |
| 35 | 11.860 |
| 40 | 13.350 |
| 45 | 14.830 |
| 50 | 16.310 |
| 55 | 17.790 |
| 60 | 19.280 |
| 65 | 20.760 |
| 70 | 22.240 |
| 75 | 23.720 |
| 80 | 25.210 |
| 85 | 26.690 |
| 90 | 28.170 |
| 95 | 29.660 |
| 100 | |

Figure 1a

Implant Selection Protocol – Four Unit Bridge

| Patient Applied Static Force | | Cantilever Length Moment Arm | | Resultant Dynamic Γ/Force | Implant Load Bearing Area (Maxilla) | Implant Load Bearing Area (Mandible) |
|---|---|---|---|---|---|---|
| pounds | X | inches | = | lbs. in. | mm² | mm² |
| 5 | X | 1.4 | = | 7 | 3.10 | 2.07 |
| 10 | X | 1.4 | = | 14 | 6.21 | 4.14 |
| 15 | X | 1.4 | = | 21 | 9.34 | 6.22 |
| 20 | X | 1.4 | = | 28 | 12.45 | 8.30 |
| 25 | X | 1.4 | = | 35 | 15.57 | 10.38 |
| 30 | X | 1.4 | = | 42 | 18.67 | 12.43 |
| 35 | X | 1.4 | = | 49 | 21.75 | 14.50 |
| 40 | X | 1.4 | = | 56 | 24.91 | 16.57 |
| 45 | X | 1.4 | = | 63 | 27.97 | 18.64 |
| 50 | X | 1.4 | = | 70 | 31.14 | 20.76 |

Implant Selection Protocol – Five Unit Bridge

| Patient Applied Static Force | | Cantilever Length Moment Arm | | Resultant Dynamic Γ/Force | Implant Load Bearing Area (Maxilla) | Implant Load Bearing Area (Mandible) |
|---|---|---|---|---|---|---|
| pounds | X | inches | = | lbs. in. | mm² | mm² |
| 5 | X | 1.84 | = | 9.2 | 4.08 | 2.72 |
| 10 | X | 1.84 | = | 18.4 | 8.16 | 5.44 |
| 15 | X | 1.84 | = | 27.6 | 12.25 | 8.16 |
| 20 | X | 1.84 | = | 36.8 | 16.33 | 10.89 |
| 25 | X | 1.84 | = | 46.0 | 20.42 | 13.61 |
| 30 | X | 1.84 | = | 55.2 | 24.50 | 16.33 |
| 35 | X | 1.84 | = | 64.4 | 28.59 | 19.06 |
| 40 | X | 1.84 | = | 73.6 | 32.67 | 21.78 |
| 45 | X | 1.84 | = | 82.8 | 36.76 | 24.50 |
| 50 | X | 1.84 | = | 92.0 | 40.84 | 27.23 |

Figure 5

DENTAL IMPLANT

FIELD OF THE INVENTION

The present invention relates to dental implant systems and, more particularly, to a screw-type dental implant system that is dynamically accommodated for different maxillary and mandibular bone densities with a predetermined radial osteocompressive force provided by adjusting the pitch of the implant thread and undersized compound angles of the tapping system to control the compression force befitting the particular bone tissue for bone lamination within physiological limits for either the maxillary or mandibular bone sites in a controlled functional osteocompressive fashion within physiologic limits.

BACKGROUND OF THE INVENTION

Dental implantology is an evolving science featuring many different implant designs. The main objective of each implant system is to provide strong and immediate fixation in the bone for the support of bridge work and other tooth prostheses. In order to establish this support, it is necessary for the dental implants to osseointegrate with the bone tissue. This osseointegration, however, has been illusive and difficult to achieve since bone does not bridge in space or move toward the implant readily, especially since connective tissue moves 0.5 mm a day following surgery and bone may take up to three months, hindered by connective tissue in the process. Hence, many different implant designs and implant techniques have been devised for the osseointegration concept.

One of the more successful dental implants systems using the process of osteocompression features a screw-type implant having a rounded thread. This implant is illustrated in U.S. Pat. No. 5,007,835, issued to Maurice Valen on Apr. 16, 1991, for DENTAL IMPLANT, incorporated herein by way of reference. The screw-type implant is threaded into a drilled and tapped hole that is prepared in the jaw bone. The osseous drilled hole is undercut by automated surgical tapping instrumentation having compound angles for bone compaction, rather than bone removal as with prior art. The rounded threads of the implant compress against the undercut surface of the tapped osteotomy, thus causing a radial osteocompressive force and bone lamination.

It has been found that this aforementioned screw-type implant has a major advantage over other implant designs due to the method of osteocompression by the implant design at the bone site. This advantage resides in the ability of the implant to provide immediate fixation in the bone within physiologic limits, placing the implant into immediate clinical function. The implant design dramatically increases the distance between the major diameter and the minor diameter of the implant, thus providing greater load bearing areas of implant support in horizontal planes at osseous sites. The radial force gives an immediate horizontal supportive function and laminates bone similar to the lamina dura of a natural tooth. This makes possible the instantaneous attachment of a tooth or a bridge superstructure to the implant abutment after surgery, placing the implant into immediate function by the patient and avoiding the loss of the laminated bone due to disuse atrophy.

This immediate functionality by design and novel surgical instrumentation clearly contrasts with blade, conventional screw, or push-in implants that often require a year or more for the bone to osseointegrate with the implant before becoming clinically functional to the patient.

More recently, it has been determined by animal studies that the radial compressive forces provided by an osteocompressive implant against the wall of the threaded bone tissue stimulate the layer of bone surrounding the prepared osteotomy. This stimulation nourishes the osteoblast cells of the bone, causing them to lay down new bone formation as demonstrated by histologic models in many renown scientific laboratories. Given occlusal force magnitude, the compressive forces exerted at the implant thread region have minimized the tension throughout the implant interface by the increase of implant region in horizontal planes and the improved bone quality at thread region by lamination. Only the radial forces provided by controlled osteocompression have been found to produce this bone stimulation and controlled functional osteocompression. Animal studies did not demonstrate bone necrosis in any of the implant sites. Conversely, animal studies for a saw-tooth-like implant did demonstrate minimal success due to sharp edges of implant areas or the lack of intimate bone contact at implant interface due to the concept of osseointegration.

The present invention seeks to improve the already successful screw-type dental implant mentioned above. It is known that bone strength varies as the bone density is different in parts of the maxillary and mandibular bone regions. The varying bone strengths make necessary the changing of the screw thread pitch to accommodate particular jaw sites based on bone quality and forces generated by the patient. This invention reflects the discovery that the pitch of the screw thread of the implant must be increased in weaker bone site areas. Whereas a lesser undercut in the bone caused by the primary tap is provided for the maxillary bone as compared to mandibular bone, attaining more support and compression for the weaker bone by the knowledge of known mechanical properties of bone and the increase by the bulk modulus of the bone against known implant load bearing areas for radial osteocompressive action by the threads the day of placement. Relatively speaking, the mechanical relationship between implant and bone can be defined by the comparative moduli of elasticity. The modulus of elasticity of trabecular bone is approximately $1.5 \times 10^6$ psi (one and one-half million), while the modulus of elasticity of cortical bone is approximately twice that of trabecular bone. The screw-type implant of the present invention is fabricated from titanium, and has a modulus of elasticity nearly five times as great as cortical bone, and ten times greater than trabecular bone where all of the endosseous implant resides. The forces imparted to the bone by the titanium implant must be in equilibrium for the implant to be successful. The size of the implant threads are also chosen relative to, and therefore dependent on, increasing the bulk modulus of bone to improve the bone's mechanical properties by controlled radial osteocompression and bone lamination.

In order to achieve dynamic balance between the implant and the weaker bone structure, it becomes necessary to provide sufficient force bearing areas of implant support in horizontal planes since implants are not physiologic, that is to say there is no physiologic attachment mechanism nor bone lamination to implant interface as with natural teeth for bone stimulation. Due to tooth extraction and disuse osseous atrophy, the weaker bone areas require more bulk support of bone in order to accommodate the disparity in the elastic moduli between the bone site and the implant interface under mastication. Ironically, the weaker bone areas of the jaw, such as in the maxillary molar regions, are also those areas sustaining greater masticatory forces.

In accordance with the present invention, greater bone support is achieved by providing a greater distance between the major and minor diameters and by increasing the pitch of the screw inversely to the bone modulus of elasticity for bone lamination and osteocompression within physiologic limits. The increased pitch allows more bone volume between implant threads, thus providing increased support in weaker bone areas. The opposite is also true, when bone in stronger (i.e., symphyseal bone) the pitch of the screw thread can be reduced as noted with the present invention for controlled radial force lamination by rounded screw threads without compromise to vascularity by over-compression.

DISCUSSION OF RELATED ART

In U.S. Pat. No. 5,628,630, issued to Misch et al, on May 13, 1997, for DESIGN PROCESS FOR SKELETAL IMPLANTS TO OPTIMIZE CELLULAR RESPONSE, a screw-type implant method is described for an osseointegrated implant. The bone contacting area of the internal diameter or "conical core section" of the screw-type implant decreases as the thread nears the "crestal end" portion, due to the decrease of the minor diameter in a conical fashion. However, there is no initial bone contact for the minor diameter at the implant "crestal end" portion along the vertical axis of minor diameter. Only 50% of the total metal-to-bone contact is provided the day of placement by the vertical thread areas which are in tension, not in compression. Without implant congruity, a failure is inevitable. Misch does not take into account that implants are not physiologic in nature. That is to say, there is no Sharpey's fibers, or biologic attachment mechanism, as with natural tooth root, to cause bone stimulation by tension. The only method of bone support by any implant is through direct bone mechanical contact, and more particular, in areas of bone support at horizontal planes as the implant's major supporting mechanism. Bone stimulation is provided by the osteocompressive action to excite cellular activity by radial forces of the thread areas as described by the present implant patent.

Although Misch attempts to claim optimization of cellular response at the implant interface, a large portion of implant interface is not in contact with bone on the day of insertion. This is due to the "conical core section" (minor diameter) being upside down or having no parallel lines. No bone stimulation can be claimed for an implant that is not in contact with bone. From the "crestal end" to the "bottom surface" (apex), the implant and parts of the threads are not initially in contact with bone, creating voids with no bone contact at implant interface. Histologically, it has been observed that connective tissue migrates into implant void spaces at 0.5 mm per day. On the other hand, bone may take three months to move an equal distance. It has also been demonstrated that if implant voids are occupied by connective tissue, bone will shy away. The fate of fibro-osseous implants has been well documented by many failure. The final osteotomy, prior to insertion of the Misch implant, is dictated by the apical end of the "bottom surface" of the upside down "conical core section." Since osteotomies are accomplished by drills of precise diameters, as described in that system, having parallel walls, nearly 50% of the Misch implant will not be in osseous contact due to the upside-down "conical core section" design.

Further, Misch does not disclose the means to ensure implant-to-bone support in a compressive mode either by design, surgery, surgical instrumentation or by synthetic bone augmentation materials the day of placement. Therefore, stress is generated at vertical implant interface, which is in shear, not in compression. In order to promote strain-induced bone growth in equilibrium, the horizontal and vertical regions of implant design must be in contact with bone to provide bone support within physiologic strain to ensure that bone at implant interface is maintained as demonstrated by analytical calculations for metal-to-bone support in equilibrium (FIG. 1a), and for specific jaw implantation (FIG. 1b).

The shape of the Misch implant threads also changes with the depth of the screw thread, wherein the thread of the implant is barrel-shaped at its crest and becomes increasingly saw-toothed as it descends into the bone. By contrast, the present invention features rounded threads that are placed in undercut, tapped and compacted bone. The threads of the present invention do not vary with depth. Rather, the implant of the current invention is provided with a given pitch for a given modulus of elasticity, to compress and laminate bone within physiologic limits, corresponding to the bone site's mechanical properties. Present invention teaches that large thread pitch for weak bone is essential for implant support since bone provides greater support if the bulk elastic modulus of bone is increased. The contrary is the teaching by U.S. Pat. No. 5,628,630, whereby small pitch is designated for spongy bone without the benefit of controlled osteocompression achieved by automated instrumentation the day of placement.

SUMMARY OF THE INVENTION

In accordance with the present invention, there is provided a screw-type implant for attaching teeth, protheses, and bridge superstructure into the mouth of an individual immediately following surgery, due to the action of osteocompression and bone lamination within physiologic limits, rather than osseointegration described by prior art. The screw-type implant has rounded threads that are screwed into a prepared cavity in the jaw bone that has been drilled and tapped in an automated and precise novel fashion. The rounded threads of the implant cause the undercut sections of the threaded bone to become compressed in a radial direction (i.e., along the plane of the thread diameter). Thread pitch of the implant is inversely dependent upon the modulus of elasticity of the bone at the implant site. As the bone modulus of elasticity decreases, the pitch of the implant screw threads increase. The thread length varies in an approximate range of between 9.0 mm to 15.0 mm, effectively increasing the load bearing area from 67.9 mm to 98.6 mm at horizontal planes. The total support area also increases from 126.6 mm, for the 9.0 mm thread, to 188.0 mm, for the 15.0 mm thread. The thread pitch and size also varies according to the bone modulus.

In threading the implant into the prepared bone site, there is caused to form a compression and lamination of the bone in contact with the rounded threads. This compression, referred to as streaming potentials, stimulates the immediate bone area and provides the area with greater blood flow and nourishment for the osteoblast cells to regenerate new bone formation. This greater nourishment stimulates the bone cells to lay down new bone mineralization. The new densified bone material surrounding the implant is laminated and provides strength and support to the surrounding implant threaded interface.

The implants of this invention feature an interchangeable abutment for receiving a threaded post occlusally. The threaded abutment can be rotated and positioned at an angle, or it can be aligned directly with the implant vertically. This allows greater flexibility in attaching artificial teeth by continuous pre-fabricated flexible bar, having no metallurgical memory by such superstructure, thus it can be adjusted to the implant abutments anywhere in the mouth. Most importantly such superstructure bar provides immediate implant splinting permitting a congruent bone formation at implant interface.

It is an object of this invention to provide an improved screw-type implant system for bone lamination and osteo-compression and a pre-fabricated bar superstructure method for immediate implant splinting in a clinical setting the day of implant surgical placement.

It is another object of the invention to provide a screw-type implant system and method that adjusts the size and pitch of the screw threads of the implant corresponding to the modulus of elasticity of the bone at the implant site.

It is another object of this invention to provide a system and a method based on the force magnitude of the patient, relevant to bone density, for the selection of specific implant's load bearing areas to attain equilibrium the day of implant placement.

It is another object of this invention to provide a method and the means to maintain bone equilibrium between specific implant design and specific bone quality by the registration of patient's force magnitude prior to implant placement as noted in FIG. 5.

BRIEF DESCRIPTION OF THE DRAWINGS

A complete understanding of the present invention may be obtained by reference to the accompanying drawings, when considered in conjunction with the subsequent detailed description, in which:

FIGS. 1a and 1b depict a numerical chart representing the modulus of elasticity (in megapascals MPa) for a specific jaw bone density region, calculating the range and quantity of metal-to-bone support required for an implant to be in equilibrium under a static occlusal force, together with a diagram showing various force-to-bone regions of the mandible and maxilla of an average jaw and areas for implantation;

FIG. 5 represents patient's applied force registration in pounds and the selection of a specific implant's load bearing areas for support required to determine equilibrium for a specific jaw and bone quality. The units of bridgework noted are used as a multiple to establish a safety factor in a clinical overload condition.

DESCRIPTION OF THE PREFERRED EMBODIMENT

Generally speaking, the invention features an improved screw-type implant that is designed to be in dynamic equilibrium relative to forces generated at the implant site. The threads of the implant vary in size and pitch relative to the modulus of elasticity for a particular bone region at which the implant is to be placed under immediate masticatory force.

Figure 1B:
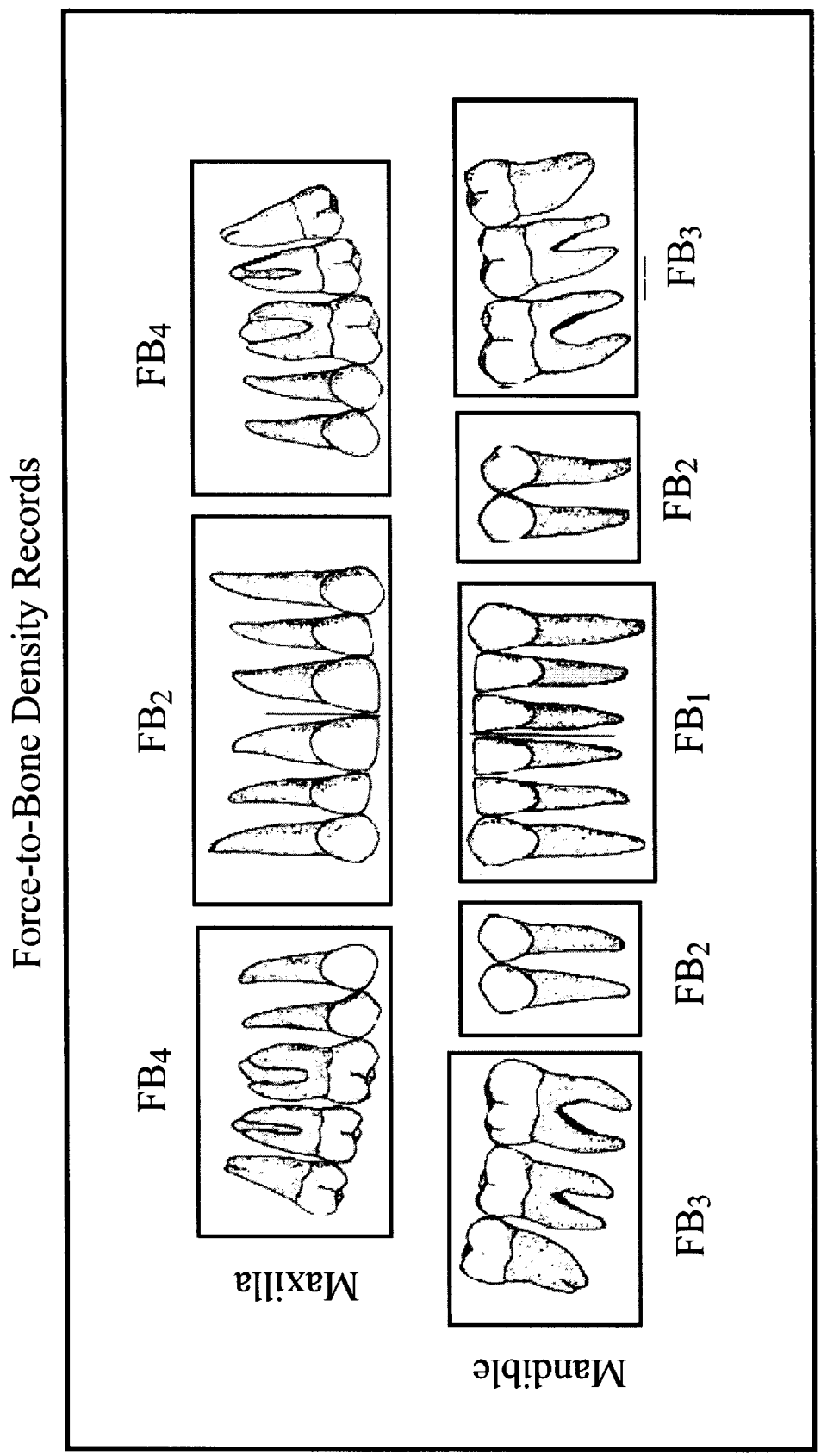

The mechanical relationship between the implant and the bone is described in units of the modulus of elasticity. Trabecular bone is $1.5 \times 10^6$ psi, while cortical bone approaches $3 \times 10^6$ psi. By contrast, the titanium of the implant has a modulus of elasticity of five times the modulus of elasticity of cortical bone: that is, $1.5 \times 10^7$ psi. It is observed that there is a mismatch in modulus of elasticity between bone and implant, especially with trabecular bone which is ten times weaker than titanium. Therefore, in areas of poorly mineralized bone, such as the $FB_4$ region of the posterior maxilla, as illustrated in FIG. 1, the implant shown in FIG. 3 is used. This implant provides an increased vertical distance between the threads compared with the implant depicted in FIG. 2. The larger bone volume accommodated in the vertical spaces between the threads offsets the differences of modulus of elasticity for the $FB_4$ bone region, thereby increasing the support at the implant site. The average masticatory force at the molar region ($FB_4$) is approximately 200 psi, compared with the bicuspid region ($FB_2$) which is approximately 100 psi in healthy individuals with full dentition. It is also to be observed that the molar fitted implant has larger threads than does the implant designed for the incisor region.

Thread pitch of the implant is inversely dependent upon the modulus of elasticity of the bone at the implant site. In other words, as the bone modulus of elasticity decreases, the pitch of the implant screw threads increase. The thread length varies in an approximate range of between 9.0 mm to 15.0 mm, effectively increasing the load bearing area from 67.9 mm to 98.6 mm. The total support area also increases from 126.6 mm, for the 9.0 mm thread, to 188.0 mm, for the 15.0 mm thread. The thread size also varies according to the bone modulus.

It is important to note that load bearing areas of most conventional implants are less than the areas of their vertical implant interface. However, due to osteocompression within physiologic limits by the implant design of this invention at the bone site, a stimulation of the osteoblast cells occurs causing the extra cellular fluids to flow over charged cell surfaces in the bone at the implant site. This bone response to such physiologic osteocompression causes the surrounding bone to strengthen and thicken due to immediate implant loading the day of surgery, avoiding disuse atrophy after bone lamination.

Figure 2:
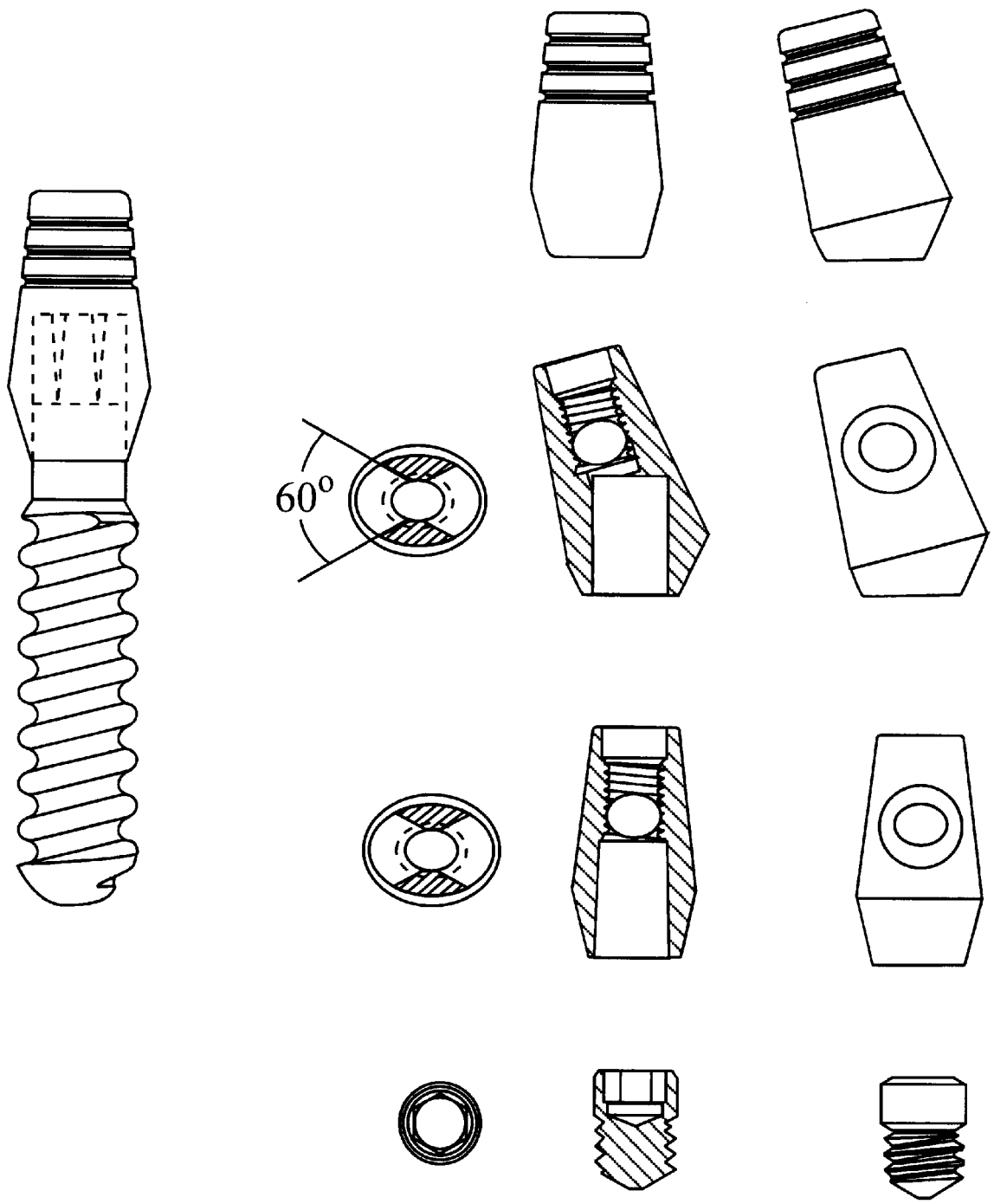
FIG. 2 illustrates a front view of a 3.3 mm diameter screw-type implant featuring the interchangeable angled abutments of this invention and straight abutment attachment apparatus for the $FB_1$ and $FB_2$ force-to-bone region shown in FIG. 1b.
Figure 3:
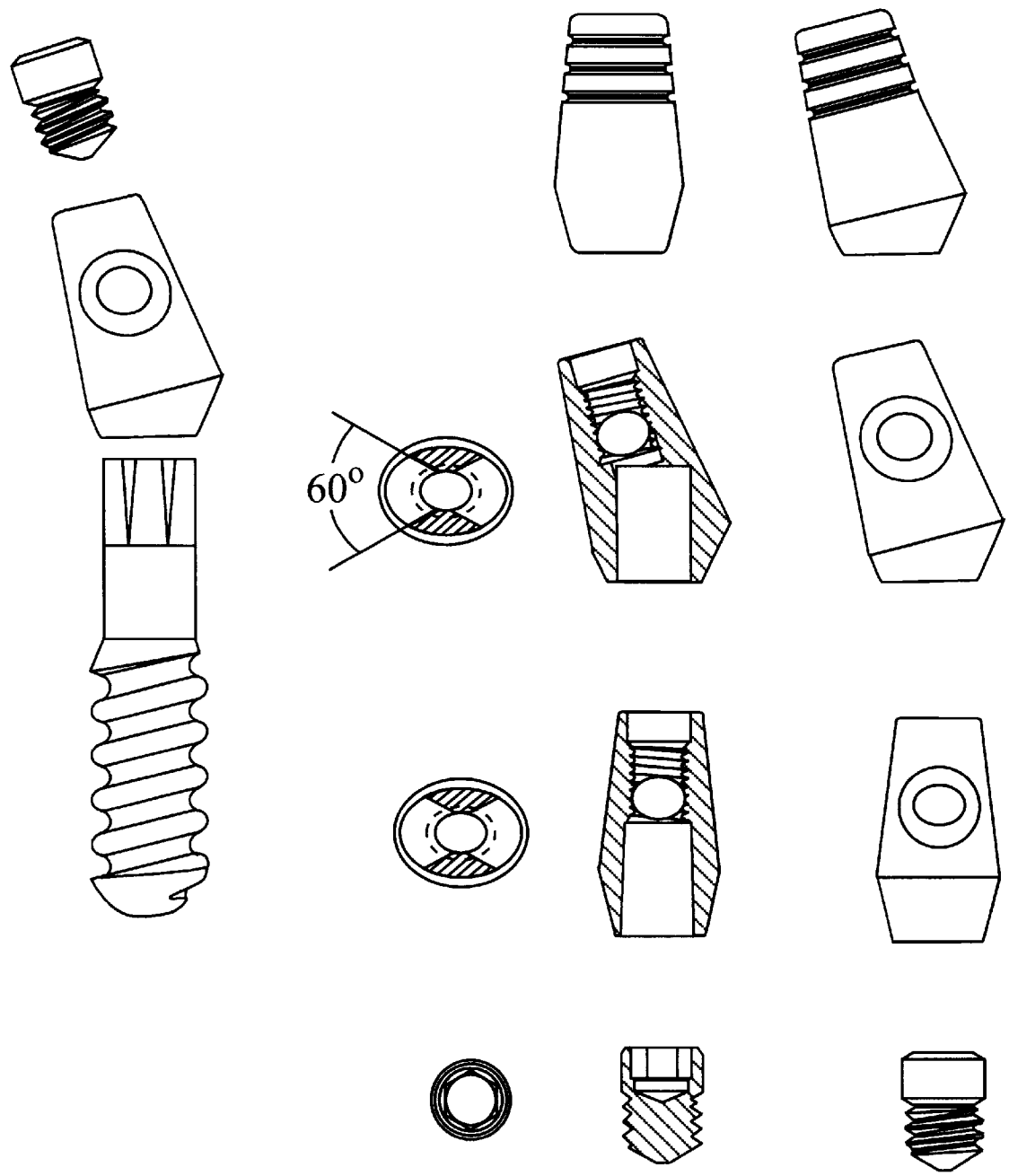
FIG. 3 depicts a front view of a 4.0 mm diameter screw-type implant featuring the interchangeable abutment for $FB_2$, $FB_3$, and $FB_4$ force-to-bone regions shown in FIG. 1b, and an abutment that is angled at 15° to the implant axis.
Figure 4:
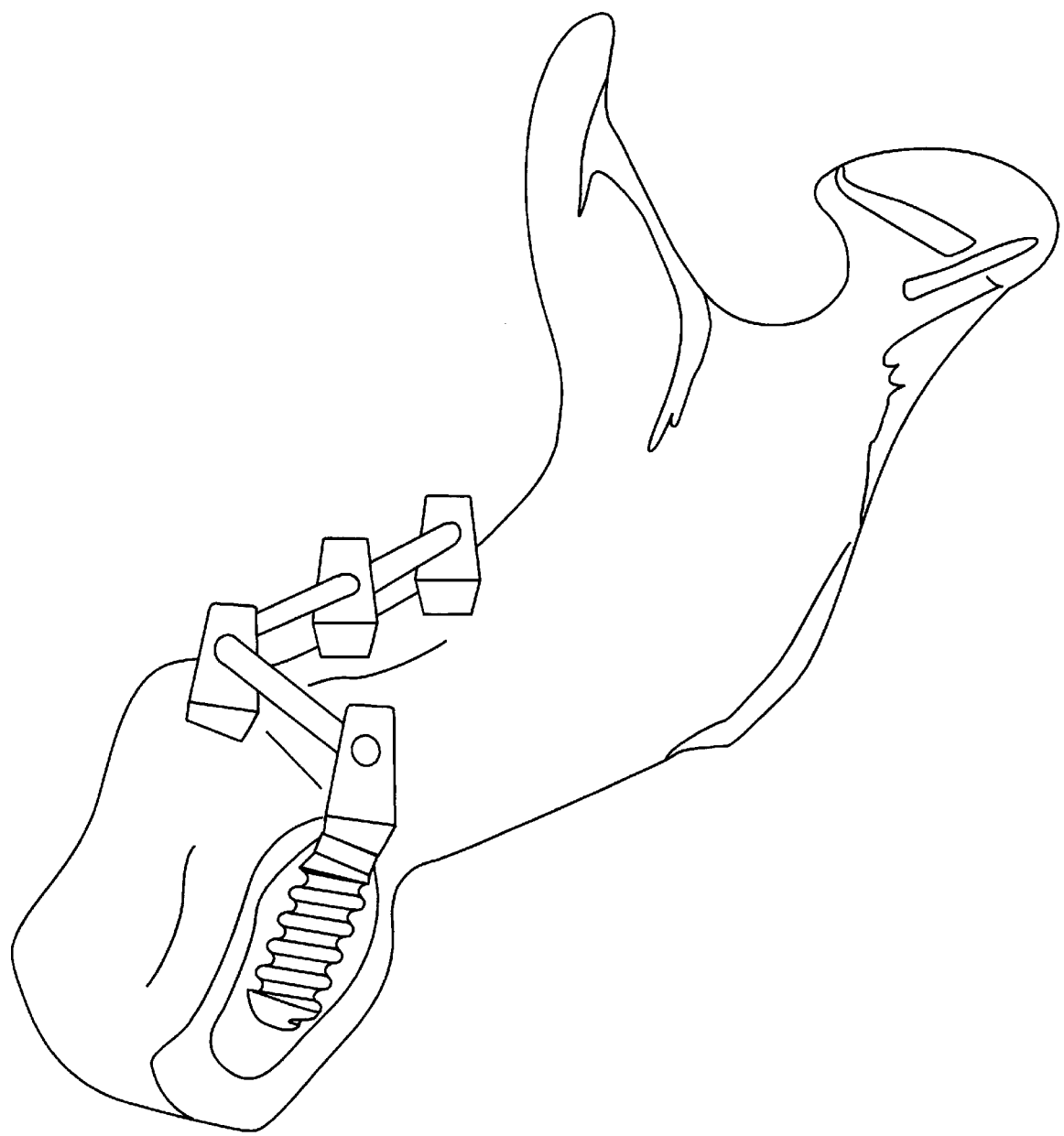
FIG. 4 shows a cross-sectional view of a portion of a jaw bone utilizing the implant and 15° angled abutment illustrated in FIG. 3, for a full denture prothesis and for the immediate implant splinting mechanism to prevent counter rotation of implants and develop better implant congruity for full denture prostheses.
Figure 6:
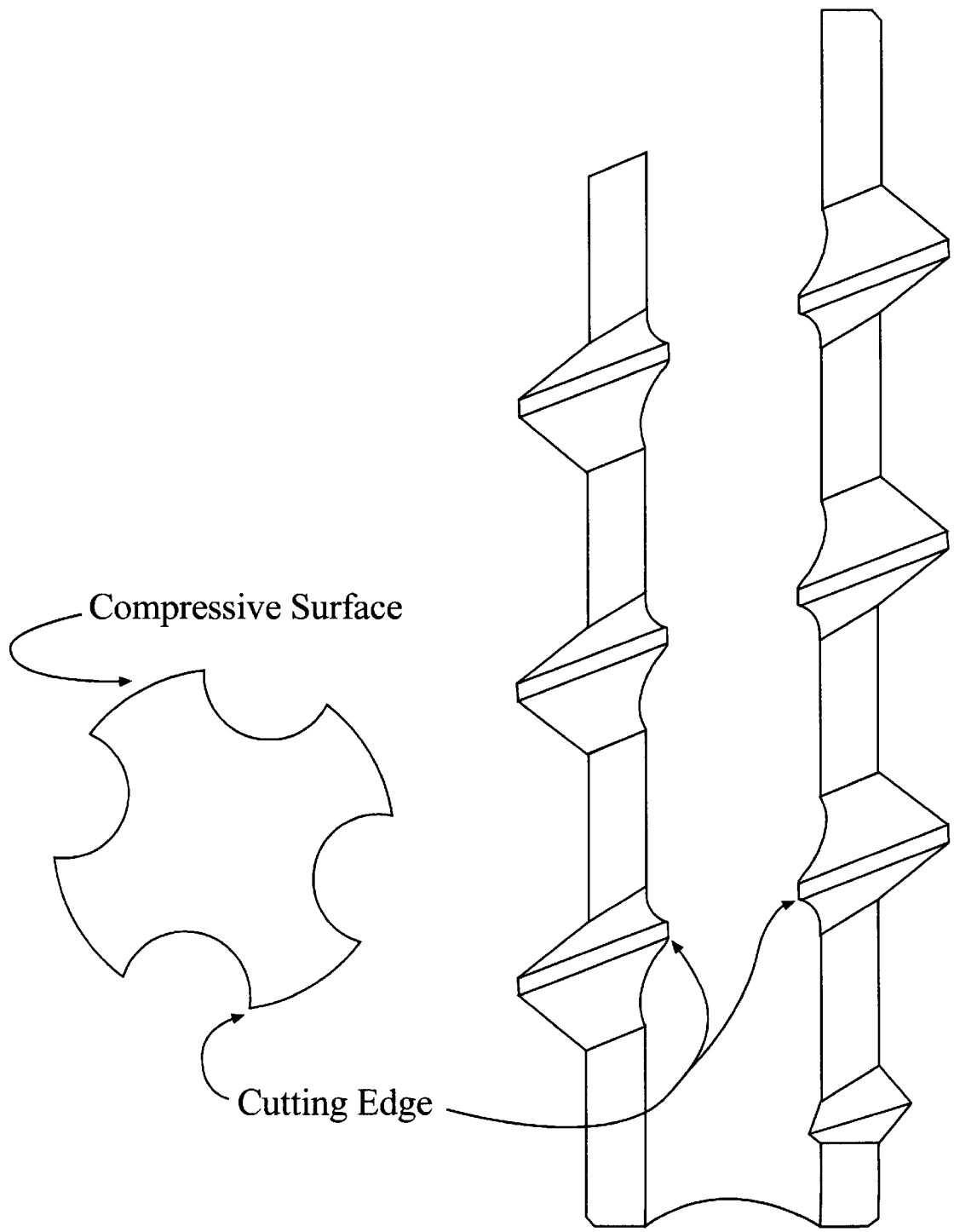
FIG. 6 represents the front view of a four-fluted tap noting the claw-like "cutting" edge, together with a bottom view of same. As the "cutting" edge indents bone on the horizontal plane, the flat surface of the tap thread compacts bone toward the osseous areas. Sequencing of taps avoids osseous trauma and provides better bone compaction without bone necrosis or removal followed by the osteocompressive action of the implant threads.

Referring to FIG. 4, a cross-section of a jaw bone is illustrated, utilizing the straight or angled abutments shown for the implant in FIG. 2. A full denture prothesis is made possible using these angled abutments in areas of implant divergence for immediate implant splinting by the bar system.

Table I, shown below, shows a comparison between various implants and the screw-type LaminOss® implant of this invention. It will be observed that of the fifteen different implants, the inventive implant provided the greatest support in the compressive mode.

TABLE I

BLADE IMPLANTS

| NAME | MESIO-DISTAL LENGTH | HEAD | VENT | APEX | GROOVES | Flexi-Cup ® | TOTAL SUPPORT AREA |
|---|---|---|---|---|---|---|---|
| Wedge Blades (Linkow) | 25.0 mm | 2.0 mm | 3.7 mm | 1.0 mm | | | 6.7 mm |
| Improved Blades (Linkow-Weiss) | 25.0 mm | 2.0 mm | 4.2 mm | 3.0 mm | | | 9.2 mm |
| Large Plate Implants | 30.0 mm | 3.0 mm | 15.0 mm | 3.7 mm | | | 21.7 mm |
| Flexi Cup ® (Valen) | 25.0 mm | 2.0 mm | 5.7 mm | 8.7 mm | 5.5 mm | 13.6 mm | 35.5 mm |
| Conventional Ramus Implant | | 4.0 mm | 30.0 mm | 2.0 mm | | | 36.0 mm |
| Improved Ramus Implant | | 6.0 mm | 37.0 mm | 4.0 mm | | | 42.0 mm |

CYLINDER AND SCREW IMPLANTS

| NAMES | DIAMETER | LENGTH | HEAD | VENT | APEX | THREADS | TOTAL SUPPORT AREA |
|---|---|---|---|---|---|---|---|
| Biotes | 5.5 mm² | 16.0 mm | 0.3 mm | 2.0 mm | 1.0 mm | 10.0 mm | 13.3 mm |
| Core-Vent | 5.5 mm² | 16.0 mm | 0.5 mm | 21.0 mm | 2.5 mm | 1.0 mm | 25.0 mm |
| Steri-Oss | 4.0 mm² | 12.0 mm | 0.5 mm | | 1.5 mm | 9.0 mm | 11.0 mm |
| TPS Screw | 4.0 mm² | 14.0 mm | | | 3.0 mm | 15.0 mm | 18.0 mm |
| DB 1000 | 4.0 mm² | 14.0 mm | | 23.0 mm | 2.0 mm | | 22.0 mm |
| Star-Vent | 4.0 mm² | 14.0 mm | | | 1.2 mm | 12.0 mm | 13.5 mm |
| LaminOss ® | 4.0 mm² | 13.0 mm | | | 10.0 mm | 40.0 mm | 50.0 mm |
| Flexi-Root | 4.0 mm² | 14.0 mm | | | 10.0 mm | 10.0 mm | 20.0 mm |
| Vent-Plant | 4.0 mm² | 14.0 mm | 0.5 mm | 3.0 mm | 3.0 mm | 12.0 mm | 18.5 mm |

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by letters patent is presented in the subsequently appended claims.

OTHER PUBLICATIONS

1. Brunski J B: "Biomechanical factors affecting the bone-dental implant interface". Clinical Materials, 10:153–201, 1992.
2. Otter M W, Palmieri V R, Cochran G V B: "Transcortical streaming potentials are generated by circulatory pressure gradients in living canine tibia". Journal of Orthopaedic Research, 8:119–126, 1990.
3. Ricci J L, Blumenthal N C, Spivak J M, and Alexander H: "Evaluation of a low-temperature calcium phosphate particulate implant material: physical-chemical properties and in vivo bone response". Journal of Oral Maxillofacial Surgery 50:969–978, 1992.
4. Roberts W E: "Bone Tissue Interface". Journal of Dental Education 52:804–809, 1988.
5. Salzstein R A, Pollack S R, Mar A F T, Petrov N: "Electro-mechanical potentials in cortical bone-I. A Continuum approach". Journal of Biomechanics 20(3):261–270, 1987.
6. Salzstein R A and Pollack S R: "Electromechanical potentials in cortical Bone-II. Experimental analysis". Journal of Biomechanics 20(3):271–280, 1987.
7. Spivak J M, Ricci J L, Blumenthal N C, Alexander H: "A new canine model to evaluate the biological response of intramedullary bone to implant materials and surfaces". Journal of Biomedical Materials Research 24:1121–1149, 1990.
8. Valen M: Surgical Manual and Prosthetic Technique Guide. Impladent Ltd., 1996.
9. Valen M and Judy K W M: Chapter 15: Flexi-Cup Three Dimensional Blade Implant Device. Endosteal Dental Implants. St. Louis, Mosby-Year Book, pp 174–187, 1991.
10. Valen M and Schulman A: "Establishment of an implant selection protocol for predetermined success". Journal of Oral Implantology 16 (3):166–171, 1990.
11. Valen M: "The relationship between endosteal implant design and function: maximum stress distribution with computer-formed three-dimensional Flexi-Cup blades". Journal of Oral Implantology 11:49–71, 1983.

What is claimed is:

1. A method of providing implant support within a jaw bone of an individual, comprising the steps of selecting a specific screw-type implant with rounded threads for a particular mandibular and maxillary region for bone lamination and osteocompression within physiologic limits, said specific screw-type implant having an increased thread pitch for weaker bone regions having lesser value of modulus of elasticity of jaw bone compared with those implants having a smaller thread pitch selected for stronger bone regions, and implanting said specific rounded thread, screw-type implant in said stronger bone regions.

2. The method in accordance with claim 1, wherein said implanted specific rounded thread, screw-type implant is also characterized as having a range of smaller rounded threads compared with those implants having larger rounded threads selected for weaker bone regions.

3. The method in accordance with claim 1, wherein said implanted rounded thread, screw-type implants are selected for different bone regions, with a thread length that varies in a range of between approximately 9.0 mm to 15.0 mm.

4. The method in accordance with claim 1, wherein said implanted rounded thread, screw-type implants have an interchangeable abutment for receiving a threaded post and a splinting superstructure mechanism.

5. The method in accordance with claim 4, wherein said interchangeable abutment for receiving a threaded post can be positioned at an angle.

6. The method in accordance with claim 4, wherein said interchangeable abutment for receiving a threaded post can be aligned directly with said interchangeable abutment.

7. The method in accordance with claim 1, wherein said implanted specific rounded thread, screw-type implant is selected for a specific bone region, together with selected tapping surgical instrumentation, said instrumentation being adapted for bone compaction in a controlled functional osteocompressive method by the radial dynamic action of said implant thread, within physiological limits relevant to the modulus of elasticity of said bone.

8. The method in accordance with claim 7, wherein said particular tapping instrumentation possesses an acute angle in one plane, adjacent a substantially flat surface for bone compaction.

9. The method in accordance with claim 8, for bone tapping and compaction, said substantially flat surface of said tap being calibrated to attain bone compaction and lamination within physiologic limits for a specific bone region.

10. A system of providing implant support within a jaw bone of an individual, comprising a plurality of selected and specific screw-type implants with rounded threads for particular mandibular and maxillary regions for bone lamination, one of said select and specific screw-type implants having an increased thread pitch for weaker bone regions having a lesser value of modulus of elasticity of jaw bone compared with those of said plurality of selected and specific implants designed for stronger bone regions.

11. The system in accordance with claim 10, wherein said implanted specific rounded thread, screw-type implant is also characterized as having larger rounded threads compared with those implants selected for stronger bone regions.

12. The system in accordance with claim 10, wherein said implanted rounded thread, screw-type implants are selected for different bone regions, with a thread length that varies in a range of between approximately 9.0 mm to 15.0 mm.

13. The system in accordance with claim 10, wherein said implanted rounded thread, screw-type implants have an interchangeable abutment for receiving a threaded post and mesio-distal horizontal receptacle of various angled configurations for immediate implant alignment and splinting mechanism.

14. The system in accordance with claim 13, wherein said interchangeable abutment for receiving a threaded post can be positioned at an angle having a horizontal receptacle of such that it possesses an internally centered bored hole of minimal contact area where the mesial and distal aspects of such bored hole are angled in a 60° outwardly fashion so as to permit a horizontal splinting bar to enter the abutment at various trajectories to facilitate alignment of all abutments with a predetermined bar apparatus secured by the threaded post of the abutment.

15. The system in accordance with claim 13, wherein said interchangeable abutment for receiving a substantially vertical threaded post can be aligned directly with said interchangeable abutment.

16. The system in accordance with claim 13, wherein said interchangeable abutment for receiving a substantially horizontal threaded post can be aligned directly with said interchangeable abutment.

17. A method of introducing a threaded implant of given size and thread pitch into a jaw of an individual, comprising the steps of:
  a) examining the jaw of an individual to determine a particular bone region requiring an implant;
  (b) matching the particular size and thread pitch of said implant to a particular bone region to excite the osteoblast cells to lay down new bone formation as determined in step (a); and
  (c) threading said matched implant of step (b) into the particular bone region of step (a), resulting in physiologic controlled stimulation and immediate bone lamination.

* * * * *